United States Patent [19]

Van der Knaap

[11] Patent Number: Plant 6,342

[45] Date of Patent: Oct. 18, 1988

[54] CHRYSANTHEMUM PLANT NAMED FRANKFORT

[75] Inventor: Jacques C. M. Van der Knaap, De Lier, Netherlands

[73] Assignee: Fides Beheer B.V., De Lier, Netherlands

[21] Appl. No.: 932,942

[22] Filed: Nov. 20, 1986

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A chrysanthemum plant named Frankfort particularly characterized by its flat capitulum form and anemone capitulum type; light pink ray florets; diameter of 50–60 mm across face of capitulum; a peripheral ring of generally tubular light pink florets surrounding yellow disc florets, and by its disease resistance.

1 Drawing Sheet

The present invention comprises a new and distinct cultivar of Chrysanthemum, botanically known as *Chrysanthemum morifolium,* Ramat., and referred to by the cultivar name Frankfort.

Frankfort is a product of a planned breeding program which had the objective of creating new chrysanthemum cultivars with anemone capitulum type, pink ray floret color, eight weeks response, disease resistance and the ability to produce commercially acceptable quality in year around cut mum programs. Such traits in combination were not present or needed improvement in previously available commercial cultivars.

Frankfort was originated from a hybridization made by applicant in a controlled breeding program in De Lier, The Netherlands in 1982. The female parent was Bijoux, disclosed in a pending application of applicant. The male parent of Frankfort was identified by the breeding identification Rosa 919. Frankfort was discovered and selected by applicant as one flowering plant within the progeny of the stated parentage in April of 1983 in a controlled environment in De Lier, The Netherlands.

The first act of asexual reproduction of Frankfort was accomplished when vegetative cuttings were taken from the initial selection in June of 1983 in a controlled environment in De Lier, The Netherlands by a technician working under formulations established and supervised by Jacques C. M. Van der Knaap. Horticultural examination of selected units initiated in October of 1983 has demonstrated that the combination of characteristics as herein disclosed for Frankfort are firmly fixed and are retained through successive generations of asexual reproduction.

Frankfort has not been observed under all possible environmental conditions. The phenotype may vary significantly with variations in environment such as temperature, light intensity and day length. The following observations, measurements and comparisons describe plants grown in De Lier, The Netherlands under greenhouse conditions which approximate those generally used in commercial practice.

The following traits have been repeatedly observed and are determined to be basic characteristics of Frankfort, which, in combination, distinguish this chrysanthemum as a new and distinct cultivar:

1. Flat capitulum form.
2. Anemone capitulum type.

3. Light pink ray florets.
4. Diameter across the face of the capitulum of 50–60 mm.
5. As the flower opens and matures, the peripheral ring of disc florets form petaloids which become open at the top and generally tubular, having the same general color as the petals.
6. Tolerance for white rust disease.

Of the many commercial cultivars known to the present inventor, the most similar in comparison to Frankfort is the maternal parent Bijoux. In comparison to Bijoux, Frankfort has smaller leaves, a faster response, much better quality in wintertime, its petals are not quilled, and it has a better tolerance to white rust disease. The flower type of Frankfort is similar to the same characteristic of Bijoux.

The accompanying color photographic drawing shows in a front view typical inflorescence and foliage characteristics of Frankfort, with colors being as nearly true as possible with illustrations of this type.

In the following description, color references are made to the Royal Horticultural Society Colour Chart. The color values were determined between 11:00 a.m. and 12:00 noon in September under natural daylight at De Lier. The Netherlands.

Classification:

*Botanical.*—*Chrysanthemum morifolium,* Ramat., cv. Frankfort.

*Commercial.*—Cut anemone spray.

INFLORESCENCE

A. Capitulum:

*Form.*—Flat.

*Type.*—Anemone.

*Diameter across face.*—50–60 mm.

B. Corolla of ray florets:

*Color (general tonality from a distance of three meters).*—Lavender pink.

*Color* ( upper surface).—75D.

*Color (under surface).*—Lighter than 75D.

C. Corolla of disc florets:

*Color.*—Yellow 13C, maturing radially outwardly to color of ray florets.

D. Reproductive organs:

*Androecium.*—Present only in disc florets; numerous.

*Gynoecium.*—Present in both ray and disc florets; numerous.

PLANT

A. General appearance:
*Height.*—70 cm.

B. Foliage:
*Color* (*upper surface*).—137A.
*Color* (*under surface*).—137B.
*Shape.*—Deeply serrated.

I claim:

1. A new and distinct chrysanthemum plant named Frankfort, as described and illustrated, and particularly characterized by its flat capitulum form and anemone capitulum type; light pink ray florets; diameter of 50–60 mm across face of capitulum; a peripheral ring of generally tubular light pink florets surrounding yellow disc florets, and by its disease resistance.

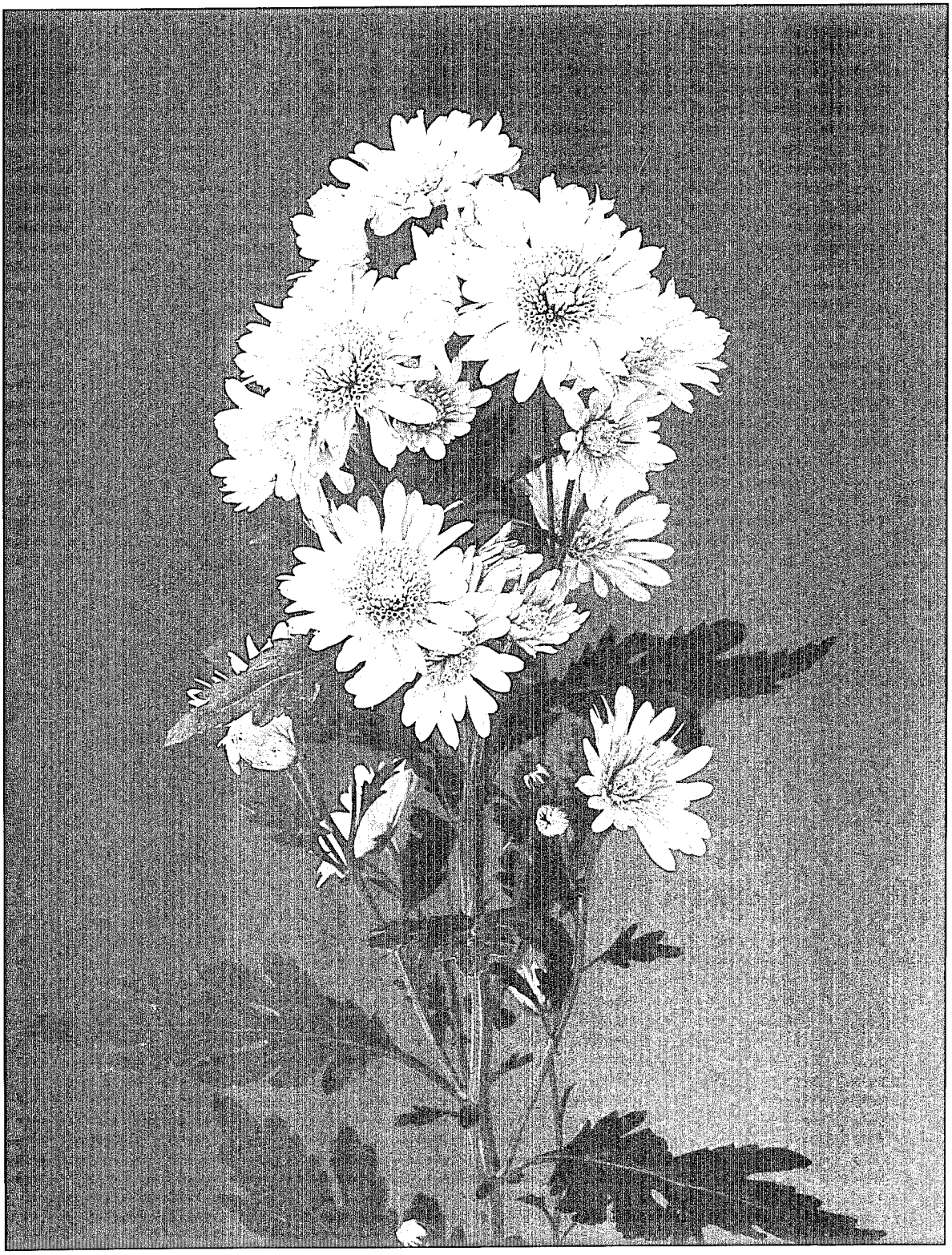

* * * * *